(12) United States Patent
Brand et al.

(10) Patent No.: US 8,865,229 B2
(45) Date of Patent: Oct. 21, 2014

(54) MARRUBIIN AND COMPOSITION FOR REDUCING SNORING, PACKAGE AND METHOD

(75) Inventors: Hans Marcel Brand, Nieuwerkerk a/d IJssel (NL); Annelize Frieda Goedbloed, Delft (NL)

(73) Assignee: Puranox Medical B.V. (NL)

( * ) Notice: Subject to any disclaimer, the term of this patent is extended or adjusted under 35 U.S.C. 154(b) by 355 days.

(21) Appl. No.: 13/218,242

(22) Filed: Aug. 25, 2011

(65) Prior Publication Data

US 2011/0305780 A1 Dec. 15, 2011

Related U.S. Application Data

(62) Division of application No. 11/997,555, filed as application No. PCT/NL2006/050194 on Aug. 4, 2006, now abandoned.

(30) Foreign Application Priority Data

Aug. 5, 2005 (NL) .................................... 1029684

(51) Int. Cl.
A01N 65/00 (2009.01)
A61K 36/53 (2006.01)

(52) U.S. Cl.
CPC ..................................... *A61K 36/53* (2013.01)
USPC ....................................................... 424/725

(58) Field of Classification Search
None
See application file for complete search history.

(56) References Cited

U.S. PATENT DOCUMENTS

| 241,144 A | 5/1881 | Lange |
| 5,591,437 A | 1/1997 | Bonte et al. |
| 5,603,935 A * | 2/1997 | Jian et al. ...................... 424/756 |
| 5,804,211 A | 9/1998 | Robertson et al. |
| 2006/0167075 A1* | 7/2006 | Pearson et al. ................ 514/406 |

FOREIGN PATENT DOCUMENTS

EP 1 201 142 A1 5/2002

OTHER PUBLICATIONS

Meyre-Silva et al., "Analgestic potential of marrubiin derivatives, a bioactive diterpene present in *Marrubium vilgare* (Lamiaceae)", "ISSN: 0014-827X, p. 3211, col. 1, paragraph 1", Apr. 17, 2004, pp. 321-326, vol. 60, No. 4, Publisher: Elsevier SAS, XP-004857599, Published in: IL Farmaco, Rome.
"US Office Action for U.S. Appl. No. 11/997,555", Jan. 11, 2010, Publisher: USPTO, Published in: US.
"US Office Action for U.S. Appl. No. 11/997,555", Jan. 14, 2009, Publisher: USPTO, Published in: US.
European Patent Office, "Written Opinion of the International Searching Authority for Intl Application No. PCT/NL2006/050194", Feb. 21, 2007, Publisher: European Patent Office, Published in: DE.
W. Knoess, "XVI *Marrubium vulgare* (White Horehound):In Vitro Culture,and the Production of Diterpene Marrubiin and Other Secondary M", "ISSN: 0934-943X, p. 274, paragraph 2", 1999, pp. 274-289, vol. 43, Publisher: Biotechnology in Agriculture and Forestry, Springer Verlag, XP-001084999, Published in: Berlin.

* cited by examiner

*Primary Examiner* — Michael Meller
(74) *Attorney, Agent, or Firm* — Kaplan Breyer Schwarz & Ottesen, LLP

(57) ABSTRACT

The invention comprises a composition for the reduction of snoring, a packaging therefor and a method for the manufacture thereof. The composition can be applied in the pharynx in different variants, in particular as spray, as gel or as foam formulation. Application of the composition at least temporarily reduces the snoring of a treated person. The invention further comprises the use of marrubiin for the manufacture of a medication for the treatment of snoring.

20 Claims, No Drawings

MARRUBIIN AND COMPOSITION FOR REDUCING SNORING, PACKAGE AND METHOD

This application claims priority to, and is a Divisional application of, U.S. patent application Ser. No. 11/997,555, with a US filing date of May 13, 2008. U.S. patent application Ser. No. 11/997,555 is a 371 filing of PCT/NL2006/050194 filed on Aug. 4, 2006, which in turn claims priority to Netherlands application number 1029684 filed on Aug. 5, 2005.

Furthermore, U.S. patent application Ser. No. 11/997,555 is incorporated herein by reference.

The invention comprises a composition for the purpose of reducing snoring. The invention further relates to a package comprising such a composition. The invention furthermore relates to a method for manufacturing such a composition. The invention also comprises the use of marrubiin for the production of a medicine for the treatment of snoring.

Snoring is the production during sleep of snorting, wheezing and/or grunting sounds during breathing. During breathing air is carried through the nose and/or oral cavity from and to the lungs via the throat and the windpipe. It is generally assumed that vibrations of tissue in the area of the pharynx are caused by the displacement of air during inhaling and exhaling, particularly in the region around the uvula and/or the vocal cords. In addition to natural predisposition, age and disorders of the oral cavity and/or pharynx, snoring is associated with, among others, use of alcohol, smoking and being overweight. The noise nuisance caused by snoring can adversely affect the sleep of other people.

The present invention has for its object to provide means with which snoring of a person can be reduced.

The invention provides for this purpose a composition for reducing snoring, comprising at least an active quantity of at least one active component with astringent properties and a physiologically acceptable excipient. Such a composition is preferably applied in the pharynx. Treatment with the composition according to the invention is found, surprisingly, to suppress the sounds of snoring, or at least reduce them to an acceptable level, and in some cases to even obviate them completely. The composition according to the invention can be applied usefully not only in the domestic domain but also in professional situations where a plurality of people must necessarily sleep in the same space, such as in a dormitory, a hospital or military barracks.

It is currently assumed that a single administration of the agent according to the invention at the beginning of the night will provide sufficient effect for the night. It cannot however be precluded that the effect diminishes after a period of time and that a new dosage of composition must be applied.

A possible explanation for the effect is that the astringent (contracting) properties of the active component or active components make the treated tissue stiffer, whereby the vibrations which cause the snoring sounds are no longer possible while the composition is active. Astringent properties are particularly understood to mean that the component applied to mucous membrane brings about a contraction of tissue at the treated location.

The physiologically acceptable excipient can be any appropriate, pharmaceutically acceptable matrix suitable for use in pharynx and oral cavity, in the form of a solid, liquid or mixture thereof. The active component can be for instance an essential oil or hydro-alcoholic botanical extract.

The mucous membrane of the oral cavity, pharynx and nasal passage to which the composition is applied is constantly producing mucus. A person will also swallow regularly, whereby the active component is also removed from the treatment location. The applied composition will thus disappear after a period of time and can therefore only act on the mucous membrane for a limited time.

It is advantageous if the composition is substantially liquid. Such a composition is simple to apply at the desired location in for instance the pharynx. A liquid composition furthermore distributes the active component properly over the surface to be treated. The liquid composition can be for instance a solution, an emulsion or a dispersion. A liquid excipient, such as water, an aqueous solution or a mixture of different liquids can be used for a liquid composition. A liquid composition can for instance be used as gargle in order to apply the active component to the desired location.

The liquid composition is preferably sprayable. A sprayable composition has a viscosity of less than 10,000 cPs, preferably less than 5000 cPs at body temperature. Such a solution can be administered using a suitable spray device. Particularly advantageous is a composition with a viscosity between 1000 cPs and 10000 cPs, preferably between 1000 and 5000 cPs. Such a composition combines a good contact time at the treated location with an efficient absorption of the active component. The active component can thus be applied in even more efficiently distributed manner. It is particularly recommended that the composition be sprayable as an aerosol, wherein a liquid is converted into a very finely distributed mist. Such a very finely distributed mist gives an even more efficient use of the composition, and is absorbed very well. The aerosol can be generated by a container with a propellant, but also by a container with a venturi spray unit.

In a preferred embodiment the composition is a gel. A gel is a liquid with an increased viscosity relative to water. Usable gel-forming excipients are generally macromolecular products which bind water. The gel preferably has a viscosity greater than 1000 cPs at body temperature. A gel provides for a longer contact time of the active component at the desired location, and results in a more efficient use of the active component and an improved effectiveness. A gel can be manufactured by adding at least one gel-forming excipient to the composition, although it is also possible to envisage the active component itself forming a gel. Usable gel-forming excipients are for instance, though not limited to, vegetable exudates such as karaya gum, tragacanth gum, arabic gum, ghatti gum, polysaccharides obtained from seeds such as guar gum, carob bean flour, tamarind gum, polysaccharides from seaweed, such as carrageenan, alginates, alginic acid, extracellular microbiological polysaccharides such as xanthan gum and dextran, starch products such as maltodextrin, maca, konjac mannan, maize starch, animal products such as casein, gelatin, keratin, cellulose derivatives such as methylcellulose, hydropropyl methylcellulose, hydroxypropyl cellulose, hydroxyethyl cellulose, copolymers of ethylene and propylene oxide, macromolecules derived from acrylic acid and/or methacrylic acid, and macromolecules derived from vinyl alcohol. For the formation of a suitable gel from such components reference is made to D. Laba, Rheological Properties of Cosmetics and Toiletries, Marcel Dekker, 1993, ISBN 0-8247-9090-1.

It is advantageous if the composition is a foam. A foam gives a highly improved distribution of the active component over the treated surface. A surface-active substance is necessary in order to make a foam. Surface-active substances reduce the surface tension of water and are always products made up of a hydrophilic (lipophobic) portion and a lipophilic (hydrophobic) portion. The surface-active substance/combination of surface-active substances can form part of the group of non-ionic, anionic, cationic of amphoteric surface-active substances. For specific components, to the extent they are suitable for use in the oral cavity and pharynx, reference is made to M. M. Rieger, Surfactant Encyclopedia, Allured Publishing Corp, ISBN #0-931710-49-9.

In a preferred embodiment at least one active component with astringent properties is white horehound. The etheric oil and/or extracts thereof are found to have particularly favourable effects on the level of snoring of a treated person. White horehound is known as marrubium vulgare (Marrubium vulgare; UK: White Horehound, D E: Andorn, F R; Marrube). White horehound contains a wide variety of physiologically active products such as flavonoids, substituted cinnamic acids such as caffeinic acid, terpenoids, osmosis-regulating products such as turicine and betonicine and pentacyclic steroids. In addition to the above-mentioned substances present in white horehound, a typical component of marrubium vulgare is the substance marrubiin, wherein marrubiin can also be present in the form of the derivatives marrubenol and marrubiol.

In another preferred embodiment at least one active component with astringent properties is black horehound. This plant and its hydrophilic extract and/or the etheric oil are also found to have particularly favourable effects on the level of snoring of a treated person. Black horehound is known as ballota nigra (Ballota nigra; UK: black horehound, FR: Ballotte fetide, DE: Gottvergess). Black horehound comprises an etheric oil consisting of flavonoids such as tangeritin, mono- and sesquiterpenoids in addition to specific typical components such as ballonigrin, ballotenol and ballotinone. These products are structurally related to marrubiin and are characterized as furanoid sesquiterpenoids (G. Savona, F. Piozzi, J. R. Hanson, M. Siverns, J. Chem. Soc., Perkin Trans., 5, 497, 1977).

It is advantageous if the composition comprises both white horehound and black horehound in active quantities. In combination with white horehound, black horehound is found to have a synergistic effect for suppressing snoring. Favourable mixtures comprise white horehound and black horehound in a mass ratio of between 1:25 and 25:1. The ratio here indicates the mass ratio of the etheric oils of respectively white horehound and black horehound.

The ratio of the percent by mass of white horehound to the percent by mass of black horehound preferably lies between 1:10 and 10:1. At such a percentage the synergistic action of the two active components is particularly efficient. The ratio of the percent by mass of white horehound to the percent by mass of black horehound more preferably lies between 1:2 and 2:1. The percent by mass of white horehound is most preferably substantially equal to the percent by mass of black horehound.

It is favourable if the composition also comprises at least one flavouring. A flavouring camouflages the taste of the combination of white horehound and black horehound, which is perceived by many people as unpleasant and bitter.

It is recommended here that the flavouring is selected from the group consisting of peppermint, aniseed and eucalyptus. These flavourings are found to be the most effective in camouflaging the taste of the combination of white horehound and black horehound. A combination of a plurality of these flavourings is also effective.

When multiple active components with astringent effect are used, an active quantity is understood to mean the quantity of all active components. The active components can therefore be present in concentrations in which they would not be individually active but which, in combination with the other components in the given concentrations, do achieve the desired effect.

It is advantageous if the composition also comprises ginger. Ginger can for instance be added as extract or etheric oil. The best-known form of ginger is Zingiber officinale, although other types have a comparable effect. An improved anti-snoring effect is obtained with ginger in combination with white horehound and/or black horehound. 20 to 60% by weight of the active components preferably consist of ginger. Such a composition moreover has a greatly improved taste, whereby a treated person perceives the treatment as pleasant and treatment with the composition can be followed with greater success.

It is recommended that the composition also comprises thyme. Such a composition gives an improved anti-snoring effect. The best-known form of thyme is known as *Thymus vulgaris*. Thyme can be incorporated as oil and/or extract in the composition. Thyme gives an improved anti-snoring effect.

It is recommended that the active components form 0.1-10% by weight of the composition, preferably 0.5-8% by weight of the formulation, more preferably 1-5% by weight. In such a concentration a good anti-snoring effect is realized, wherein the active components are moreover used efficiently. A part of the effective component is after all removed from the desired location after a time by the production of mucus by the mucous glands in combination with swallowing, and can therefore only act on the treated location for the limited contact time. At higher concentrations a large part of the active component is in fact not used to achieve the anti-snoring effect, and this is in fact a waste of the often relatively expensive active components. At the stated concentrations it is possible to apply the active component in well distributed manner so that it can act sufficiently on the mucous membrane at the treated location during the contact time.

The composition preferably also comprises an active quantity of osmosis regulator. Addition of an osmosis regulator is found to improve the anti-snoring effect of the composition. The best anti-snoring results are achieved with formulations comprising between 0.1 and 10% by weight of osmosis regulator, depending on the matrix used. It is possible here to use a combination of different substances as osmosis regulator. Osmosis regulators are products which are responsible for the intercellular transport of water (E. E. Brand-Garnys, H. M. Brand, Soap, Perfumery and Cosmetics, 2005). Excessive water transport results in slackening of the tissue, which encourages snoring, and this is prevented by the osmosis regulator. Osmosis regulators which can be used are betaine (trimethylglycine) and related amino acid betaines such as alanine betaine, dimethylsulfoniopropionate (DMSP; S,S-dimethyl-3-mercaptopropionic acid), choline sulfate, proline and hydroxyproline, betaine, ectoine, some polyoles such as glycerol and non-reducible sugars such as trehalose, mannitol and inositol.

In a preferred embodiment the osmosis regulator substantially comprises betaine. Addition of betaine as osmosis regulator is found to give improved anti-snoring results as well as an improved sensation when administered orally. This could be because betaine improves the absorption of the active component at the treated location. The systematic name of betaine is trimethylglycine (TMG).

It is advantageous if the composition comprises 1 to 20% by weight of a permeability enhancer. A permeability enhancer accelerates the absorption of the active component by the treated tissue, and thereby the effectiveness of the formulation. Ethanol, dimethyl sulfoxide (DMSO), phytantriol and methyl sulfonyl methane (dimethyl sulfone; MSM), or mixtures thereof are particularly useful as permeability enhancer.

The composition preferably also comprises at least one flavouring. Using the flavouring the taste of the composition can be improved, whereby a treated person perceives the treatment as being more pleasant. The flavouring is preferably an etheric oil or a mixture thereof. At least one flavouring is preferably chosen from the group consisting of eucalyptus oil, menthol, oil of cloves, aniseed oil and peppermint oil. Other etheric oils can also be envisaged, such as sweet orange oil, pine oil, grapefruit oil and mandarin oil. These substances cause a fresh and tasty sensation in the mouth and throat. Combinations of multiple types of flavouring can be envisaged. The flavouring generally comprises between 0.01 and 5% by weight of the formulation, depending on the type of flavouring and the desired strength. The frequently bitter or otherwise less agreeable taste of the active component is thus camouflaged in effective manner. This is particularly advantageous if the composition comprises thyme, the bitter taste of which can be camouflaged by flavourings.

It is advantageous that the composition comprises between 0.5 and 5% by weight of xylitol. Xylitol has an antibacterial action, whereby the user of the composition has relatively fresh breath once the active duration has ended. In addition, xylitol also acts as sweetener, thereby enhancing the taste of the composition.

The composition preferably also comprises 0.0 1-5% by weight of bio-adhesive gelling agent. A longer contact time of the composition at the desired location is hereby obtained. At high concentrations of gelling agent (0.0 5-5% by weight) a gel is obtained with high viscosity, this likewise contributing toward an increased contact time at the treated location. Gelling agents with bio-adhesive properties that can be used comprise for instance hydroxypropyl methylcellulose, xanthan gum, karaya gum, tragacanth gum, carrageenan, mannan gum and chitosan.

It is advantageous when the composition also comprises 0.01-2% by weight of surfactant. A surfactant is a surface-active substance and contributes toward efficient distribution of the active component over the treated surface. A surfactant is also essential for obtaining a foam formulation. The surface-active substance to be applied can comprise any physiologically and pharmaceutically acceptable surfactant of combination thereof, including non-ionic, anionic and amphoteric surface-active substances such as alkyl-substituted polyglucose (n=1-3), anionic derivatives thereof such as sodium cocopolyglucose tartrate, fatty acid esters of lactic acid, lactylates, and polysorbates.

The invention also provides a packaging comprising a composition according to any of the foregoing claims, and dosing means adapted for oral administration of the composition. The package is preferably also provided with dosing means. Depending on the form of the composition (solid, liquid, gel, emulsion) this can be for instance an atomizer, spray or gel dispenser.

It is advantageous if the dosing means comprise guide means adapted to guide the composition to the pharynx of a person for treating. It is possible here to envisage a flexible hose with which for instance a liquid can be deposited at the desired location in the pharynx. The composition can in this way be used as efficiently as possible.

Yet another preferred embodiment provides the measure that the package comprises a container which comprises a propellant in addition to the composition. Convenience of use is hereby greatly enhanced.

Use can herein be made of a pressurized container wherein the propellant is held in a flexible vessel in the container. This is known as the so-called two-chamber system. The propellant does not exit to the outside here, so there is a greater choice of propellant. Propellant is understood to mean a gas under pressure. This is preferably a pharmacologically acceptable gas or gas mixture, such as compressed air, nitrogen or carbon dioxide.

According to yet another embodiment, the package is provided with a valve adapted for placing between the lips. It is hereby easy to reach the parts at the back of the pharynx to be contacted with the composition, such as the uvula, by means of an aerosol beam.

The same effect is also achieved when the package is provided with a spout for guiding the composition to the pharynx.

The invention further provides a method for manufacturing a composition for treatment of snoring according to the invention, comprising of mixing at least one active component with astringent properties and a physiologically acceptable excipient. In addition, other possible pharmaceutically acceptable additives as referred to above can also be added so as to obtain the desired composition.

The invention also provides for the use of marrubiin for the manufacture of a medication for the treatment of snoring. Marrubiin is found to have a particularly good anti-snoring effect. Marrubiin is also understood to include the oxidation products marrubenol and marrubiol directly obtainable from marrubiin, and other possible synthetic and natural derived substances such as esterified products. Marrubiin is present in 0.3-1.0% by weight in white horehound and can be extracted therefrom as hydrophilic extract or etheric oil. The extracts or oils of white horehound usually comprise marrubiin as mixture with marrubenol and marrubiol. The systematic name of marrubiin is 6-(2-furan-3-yl-ethyl)-6-hydroxy-2a,5a,7-trimethyldekahydronafto[1,8-bc]furan-2-on. The chemical structure of marrubiin is shown below.

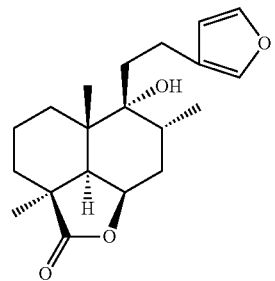

The invention will now be elucidated with reference to the following examples.

The formulations A, B and C in table 1 are found to have a good anti-snoring effect when applied in the pharynx via the mouth. All formulations are based on water: the shown percentages by weight are thus supplemented to 100% with water. Composition A is a liquid composition which can be used for applying with a spray or as droplets. Composition B is a gel formulation. Composition C is a foam.

TABLE 1

|  | A | B | C |
| --- | --- | --- | --- |
| white horehound | 5 | 5 | 5 |
| black horehound | 5 | 5 | 5 |
| thyme oil | — | 0.1 | 0.1 |
| ginger oil | 0.15 | — | 0.15 |
| eucalyptus oil | 0.05 | 0.1 | 0.05 |
| peppermint oil | 0.15 | 0.15 | 0.15 |
| xylitol | 3.6 | 3.6 | 5 |

TABLE 1-continued

|  | A | B | C |
|---|---|---|---|
| betaine | 3 | 3 | 3 |
| oleth-20 | 0.8 | 0.6 | 1 |
| pyridoxine HCl | 0.5 | 0.6 | 0.7 |
| dimethyl sulfone | 3.5 | 5 | 3.5 |
| hydroxypropyl methylcellulose | — | 0.6 | — |
| sodium cocopolyglucose tartrate | — | — | 0.8 |
| Water | To 100% | To 100% | To 100% |

The quantities of substances in table 1 are stated in percent by weight. White horehound, black horehound, thyme, ginger, eucalyptus and peppermint can be added as essential oil, extract or tincture. The percentages by weight of thyme, ginger, eucalyptus and peppermint in table 1 relate to the etheric oils. White horehound, black horehound, ginger and thyme can be considered the most important active components for the anti-snoring effect. Eucalyptus oil, peppermint oil and MSM can be effectively deemed as substances contributing toward the desired effect. Eucalyptus oil, peppermint oil, xylitol also have a function as flavouring, wherein xylitol also has a (limited) microbiological activity. Betaine is added as osmosis regulator. Oleth-20 is a non-ionic surfactant which also has a function as solubilizing agent for essential oils. Pyridoxine is also known as vitamin B6 and helps to prevent mucous membrane irritations and has expectorant (mucus-dissolving) properties. The addition of a mucus-dissolving compound in an active quantity also contributes toward the anti-snoring effect. Hydroxypropyl methylcellulose is a gelling agent which also has bio-adhesive properties. Sodium cocopolyglucose tartrate is a foaming agent and is only present in the foam formulation C. All compositions are supplemented to 100% with water. The compositions are obtained by mixing the ingredients at suitable temperature and with suitable techniques.

It will be apparent that many preferred variants of the composition according to the invention can still be envisaged.

What is claimed is:

1. A method for reducing snoring in a person in need thereof, the method comprising:
administering, to the person in need thereof, a composition in a pressurized container, wherein the composition in the pressurized container comprises a therapeutically effective amount of a white horehound extract and a black horehound extract for reducing the snoring of said person in need thereof.

2. The method as claimed in claim 1, wherein the composition is substantially liquid.

3. The method as claimed in claim 1, wherein the composition is a gel.

4. The method as claimed in claim 1, wherein the composition is a foam.

5. The method as claimed in claim 1, wherein the white horehound extract is an active component with astringent properties.

6. The method as claimed in claim 1, wherein the black horehound extract is an active component with astringent properties.

7. The method as claimed in claim 1, wherein a ratio of the percent by mass of the white horehound extract to the percent by mass of the black horehound extract lies between 1:10 and 10:1.

8. The method as claimed in claim 7, wherein a ratio of the percent by mass of white horehound extract to the percent by mass of the black horehound extract lies between 1:2 and 2:1.

9. The method as claimed in claim 1, wherein the percent by mass of the white horehound extract is substantially equal to the percent by mass of black horehound extract.

10. The method as claimed in claim 1, wherein the composition also comprises at least one flavouring, and wherein the flavouring is an etheric oil.

11. The method as claimed in claim 10, wherein the flavouring is selected from the group consisting of peppermint, aniseed and eucalyptus.

12. The method as claimed in claim 5, wherein the composition also comprises ginger.

13. The method as claimed in claim 5, wherein the composition also comprises thyme.

14. The method as claimed in claim 1, wherein the active components form 0.1-10% by weight of the composition.

15. The method as claimed in claim 1, wherein the composition also comprises an active quantity of osmosis regulator.

16. The method as claimed in claim 15, wherein the osmosis regulator substantially comprises betaine.

17. The method as claimed in claim 1, wherein the composition comprises 1 to 20% by weight of a permeabilizer.

18. The method as claimed in claim 1, wherein the composition comprises between 0.5 and 5% by weight of xylitol.

19. The method as claimed in claim 1, wherein the composition also comprises 0.01-5% by weight of bio-adhesive gelling agent.

20. The method as claimed in claim 1, wherein the composition also comprises 0.01-2% by weight of surfactant.

* * * * *